US00PP12337P2

(12) United States Plant Patent
Heims

(10) Patent No.: US PP12,337 P2
(45) Date of Patent: Jan. 8, 2002

(54) PULMONARIA PLANT NAMED 'HIGH CONTRAST'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/628,782

(22) Filed: Jul. 31, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Pulmonaria plant characterized by a unique combination of silver leaves with a dark green margin, sporadic green blotches in the silver, and irregularly ruffled leaves.

2 Drawing Sheets

The present invention relates to a new and distinct hybrid of Pulmonaria, of the family Boraginaceae, which originated as a cross between Pulmonaria 'Berries and Cream' U.S. Plant Pat. No. 10,597 (seed parent) and an unknown pollen parent. This is known to be an outcross because Pulmonaria does not normally self pollinate. Due to the fact that the instant plant and parent plants are of hybrid origins, no species designations are given.

This new Pulmonaria is a result of an open-pollinated cross of the aforementioned plants in Canby, Oreg. This hybrid was selected from a large selection of seedlings. The seed parent plant was retained to observe habit and to compare with the instant plant. The new variety has been reproduced only by asexual propagation (division and tissue culture). Each of the progeny exhibits identical characteristics to the original plant.

This plant is characterized by the following:

1. Silver foliage edged with a dark green margin.
2. Sporadic dark green blotches occurring in the silver area.
3. Irregularly ruffled leaves and margins.
4. Low mounding habit when in bloom.
5. Vigor.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

The drawings show Pulmonaria 'High Contrast' in Canby, Oreg.

DETAILED PLANT DESCRIPTION

Figure 1:
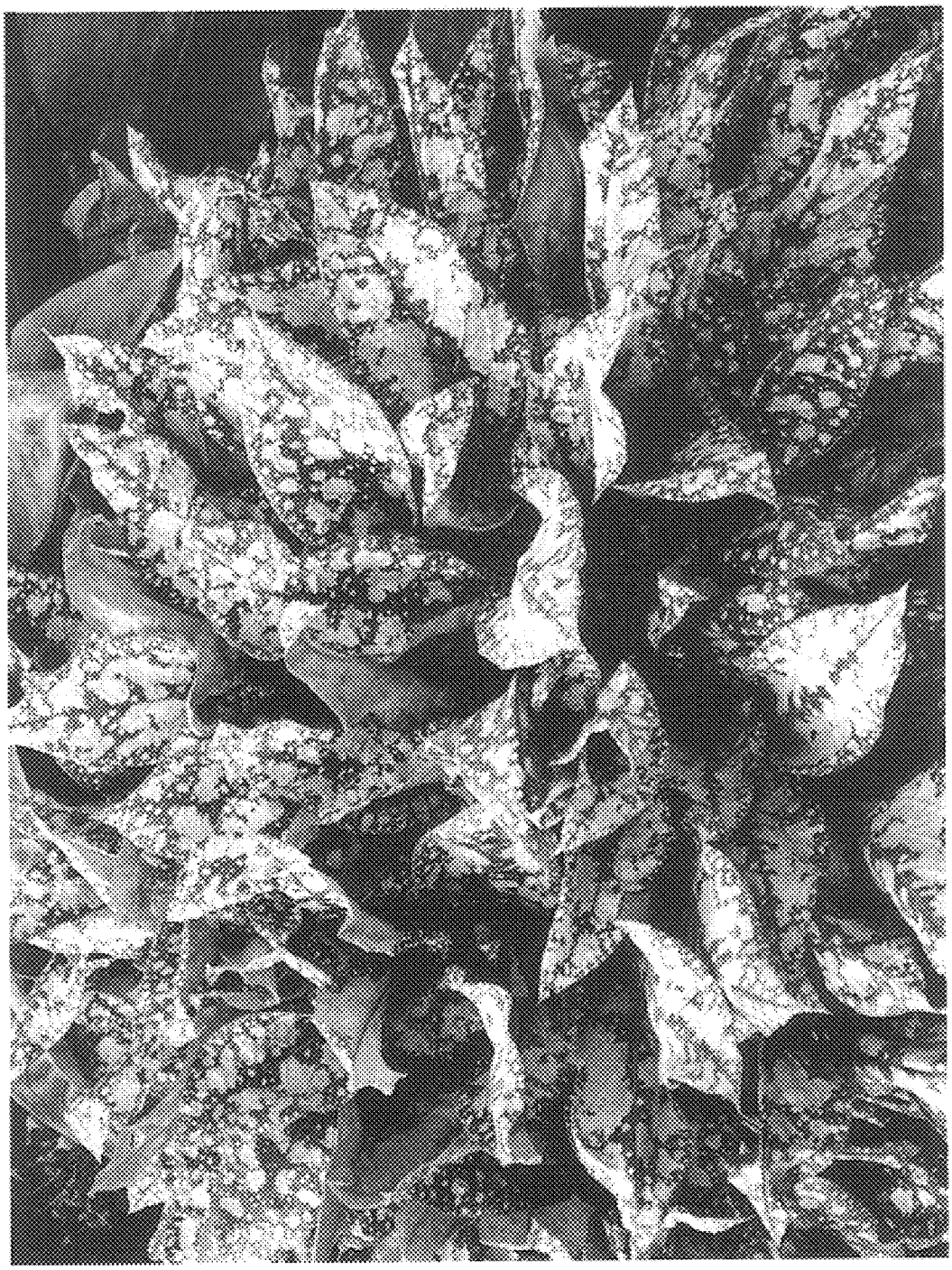
FIG. 1 shows an adaxial and abaxial views of the leaf of 'High Contrast'.
Figure 2:
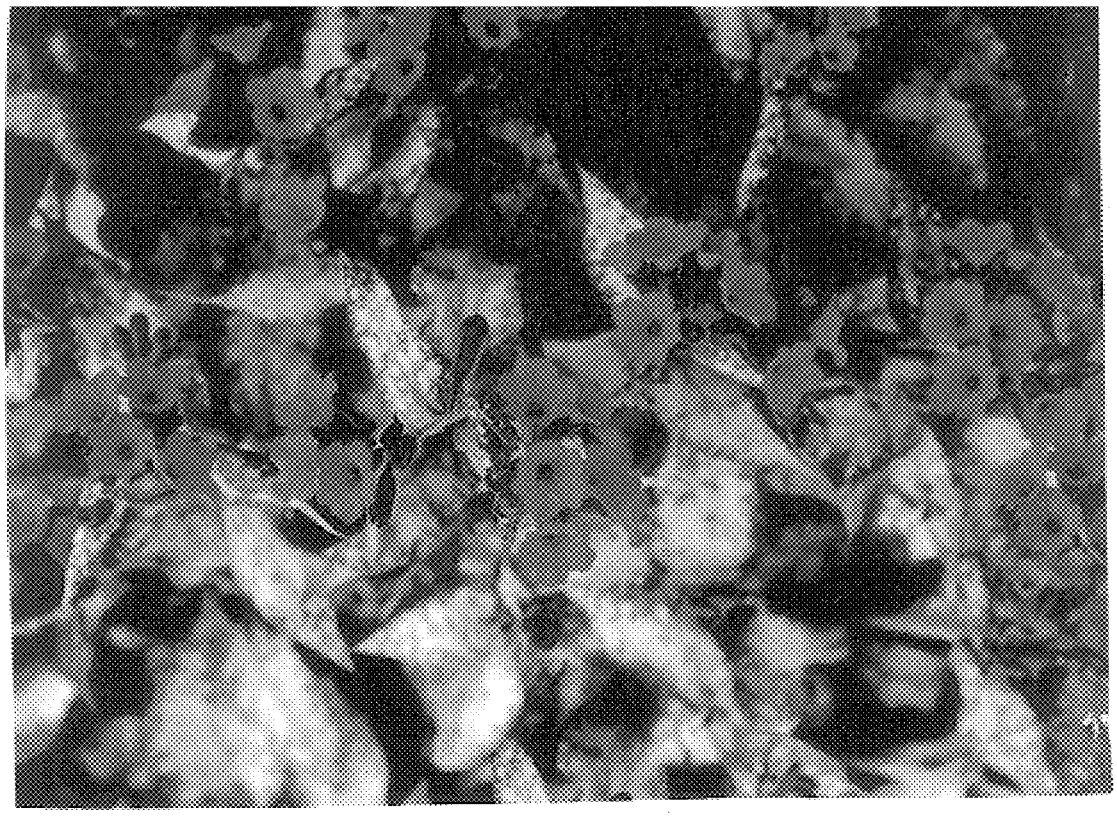
FIG. 2 shows the flowers of 'High Contrast'.

The following is a detailed description of the new Pulmonaria hybrid based on observations of one and a half year old specimens grown in a pot in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—65 cm wide and 26 cm tall.
- *Form.*—Basal clump.

Foliage:
- *Type.*—Simple.
- *Shape.*—Ovate to oblong.
- *Blade length.*—To 22 cm.
- *Blade width.*—To 9.5 cm.
- *Petiole length.*—15–20 cm.
- *Margins.*—Entire, ciliate, irregularly undulating.
- *Apex.*—Narrowly acute.
- *Base.*—Attenuate.
- *Leaf texture.*—Setose. Slight, irregular rugosity.
- *Petiole texture.*—Setose.
- *Leaf arrangement.*—Rosette.
- *Venation.*—Reticulate-pinnate.

Flower bud:
- *Size.*—1.4 cm deep and 0.4 cm wide.
- *Description.*—Ovoid shape, about 0.4 cm exposed from calyx.

Flower:
- *Type.*—Complete. Perfect.
- *Shape.*—Funnelform to salverform.
- *Size.*—1.8 cm deep and 1.4 cm wide.
- *Corolla.*—5 fused petals with rounded lobes.
- *Calyx.*—5 fused sepals, tubular campanulate, parted ⅓ to the base, hirsute and with glandular hairs.
- *Calyx size.*—1.4 cm deep and 0.9 cm wide.
- *Pistil.*—Pin type, exerted from corolla.
- *Ovary position.*—Partly inferior.
- *Carpel number.*—4.
- *Stamen number.*—5, in the corolla tube.
- *Inflorescence type.*—Forked cymes.
- *Peduncle width.*—3 mm tapering to 1 mm.
- *Peduncle texture.*—Setose.
- *Bloom period.*—Late February to early April.
- *Fragrance.*—None.

Seed:
- *Type.*—4 smooth nutlets, oval in shape, black and shiny.
- *Fertility.*—Fertile.

Disease: None have been observed on plants grown commercially in Canby, Oreg.

COLOR CHARACTERISTICS

Foliage:

*Upper surface.*—RHS 192A Greyed-Green Group.

*Upper surface, edge and sporadic patches in center.*—RHS 139A Green Group.

*Lower surface.*—RHS 138B Green Group.

Flower:

*Bud.*—RHS 146B Red-Purple Group.

*Corolla.*—RHS 70A Red-Purple Group to RHS 94A Violet-Blue Group.

*Calyx.*—RHS 146C Yellow Green Group.

*Pollen.*—RHS 155D White Group.

Seed: RHS 202A Black.

DESCRIPTION OF PARENT PLANTS

The instant plant resulted from an open-pollinated cross between Pulmonaria 'Berries and Cream' U.S. Plant Pat. No. 10,597 and an unknown pollen parent. Pulmonaria 'Berries and Cream', as described in U.S. Plant Pat. No. 10,597, has markedly ruffled leaves, silver with a thin green margin, and distinctive raspberry-pink flowers in spring. The instant plant differs in having sporadic green blotches in the silver area, wider green margin, and irregularly ruffled leaves and margins.

Compared to Pulmonaria 'Dark Vader' (U.S. Plant Patent application Ser. No. 09/628,783), the instant plant has more silvering on the leaves, a taller habit, and a pin type pistil (exerted from the corolla tube) rather than a thrum type (included in corolla tubes).

I claim:

1. A new and distinct hybrid of Pulmonaria plant substantially as shown and described, characterized by a unique combination of silver leaves with a dark green margin, sporadic green blotches in the silver area, and irregularly ruffled leaves.

* * * * *